United States Patent [19]

Hung

[11] Patent Number: 4,908,461

[45] Date of Patent: Mar. 13, 1990

[54] PROCESS FOR DECHLORINATING 4,5-DICHLOROFLUORODIOXOLANES TO OBTAIN FLUORODIOXOLES

[75] Inventor: Ming-Hong Hung, Wilmington, Del.

[73] Assignee: E. I. Du Pont De Nemours and Company, Wilmington, Del.

[21] Appl. No.: 274,955

[22] Filed: Nov. 28, 1988

Related U.S. Application Data

[63] Continuation-in-part of Ser. No. 135,396, Dec. 31, 1987, abandoned.

[51] Int. Cl.[4] .............................................. C07D 317/42
[52] U.S. Cl. ..................................................... 549/455
[58] Field of Search ........................................ 549/455

[56] References Cited

U.S. PATENT DOCUMENTS

| | | | |
|---|---|---|---|
| 3,865,845 | 2/1975 | Resnick | 549/455 |
| 4,393,227 | 7/1983 | Squire | 549/455 |
| 4,429,143 | 1/1984 | Anderson et al. | 549/455 |
| 4,485,250 | 11/1984 | Squire | 549/455 |
| 4,535,175 | 8/1985 | Squire | 549/455 |

OTHER PUBLICATIONS

Olah et al., Synthesis, 607 (1976).
Dairs et al., ibid., 1027 (1984).
Sato et al., ibid., 1025 (1982).

*Primary Examiner*—Nicky Chan

[57] ABSTRACT

Process for preparing dioxoles by dechlorinating 4,5-dichlorodioxolanes with selected molar quantities of a lithium aluminum hydride/titanium (III or IV) chloride reagent at 20°–35° C.

3 Claims, No Drawings

PROCESS FOR DECHLORINATING 4,5-DICHLOROFLUORODIOXOLANES TO OBTAIN FLUORODIOXOLES

CROSS-REFERENCE TO RELATED APPLICATION

This is a continuation-in-part of application No. 07/135,396 filed Dec. 21, 1987, now abandoned.

BACKGROUND OF THE INVENTION

New methods for obtaining fluorodioxoles are of interest because of their increased use as monomers for the preparation of fluoropolymers.

Mixtures of lithium aluminum hydride, $TiCl_3$ or $TiCl_4$, and tetrahydrofuran have been shown to be efficient reagents for dehalogenating vic-dihalo-organic compounds to obtain the corresponding olefin when the reagents and the vic-dihalo compound are refluxed. (See Olah et al, *Synthesis*, 607 [1976]). However, when such reagents are refluxed with 4,5-dichlorofluorodioxolanes, the yield of the corresponding fluorinated dioxole is very low.

SUMMARY OF THE INVENTION

It has now been found that if the ratio of $LiAlH_4$ to $Ti(Cl)_x$ wherein x is 3 or 4 is increased and the temperature of the dehalogenation reaction is lowered, the yield of the corresponding fluorinated dioxole is increased to a surprising degree.

Accordingly, this invention resides in a process for preparing a dioxole of the formula

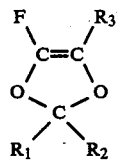

wherein $R_1$ and $R_2$ are each independently selected from the class consisting of fluorine, chloroalkyl, chlorofluoroalkyl, and fluoroalkyl of 1-3 carbon atoms, and $R_3$ is F, Cl or perfluoroalkyl of 1-3 carbon atoms, by dechlorinating the dioxolane of the formula

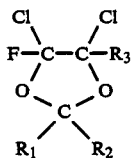

wherein $R_1$, $R_2$ and $R_3$ are as defined above, which process comprises:

A. adding lithium aluminum hydride and $TiCl_x$ wherein x is 3 or 4 to tetrahydrofuran at a molar ratio of lithium aluminum hydride to $TiCl_x$ of 2:1 to 8:1, and mixing the components at 0° C. to the reflux temperature of the mixture, preferably for 15-120 minutes;

B. mixing the dioxolane into the mixture prepared in Step A until the molar ratio of the dioxolane to the titanium chloride is 1:1 to 4:1, preferably about 2:1, at a temperature of 20°-35° C.; and C. isolating the dioxole formed in Step B.

DETAILED DESCRIPTION OF THE INVENTION

The lithium aluminum hydride ($LiAlH_4$), the $TiCl_3$ or $TiCl_4$, and the tetrahydrofuran are all well known chemical reagents and need no further description. The dioxolanes used herein can be prepared as generally described in U.S. Pat. No. 3,865,845. They can be exemplified by 4,5-dichloro-4,5-difluoro-2,2-bis(trifluoromethyl)-1,3-dioxolane; 4,5-dichloro-2,4,5-trifluoro-2-pentafluoroethyl-1,3-dioxolane; 4,5-dichloro-4,5-difluoro-2-pentafluoroethyl-2-trifluoromethyl-1,3-dioxolane; 4,5-dichloro-4,5-difluoro-2,2-bis(chlorodifluoromethyl)-1,3-dioxolane; 4,5-dichloro-5-fluoro-2,2,4-tris(trifluoromethyl)-1,3-dioxolane; 4,5-dichloro-2,4,5-trifluoro-2-heptafluoropropyl-1,3-dioxolane; and 4,5-dichloro-4,5-difluoro-2,2-bis(pentafluoroethyl)-1,3-dioxolane.

The reagent mixture preferred in step A of the process of the invention is different from that described in Olah et al, supra, as being useful to dehalogenate certain compounds. Olah et al disclose a molar ratio of $LiAlH_4$ to $TiCl_x$ of 1:2, rather than 2:1 to 8:1 as required herein.

It has been found that in order to effectively remove adjacent chlorine atoms, different amounts of ingredients must be used, than in Olah et al, and, preferably, the contact temperature must be lower. As noted, the ratio of $LiAlH_4$ to $TiCl_x$ must be 2:1 to 8:1, preferably 3:1 to 6:1. Preferably, the $LiAlH_4$ is added to the tetrahydrofuran first. The addition of $TiCl_x$ is preferably made slowly while cooling the mixture. To effectively reduce the $TiCl_x$ to the activating level, the mixture can be refluxed, if desired. Thus, the mixing temperature may be in the range 0° C. to the reflux temperature of the mixture. Total time of mixing, including any refluxing, will preferably be 15 to 120 minutes. The optimum time, temperature and pressure can readily be determined by one skilled in the art.

The $LiAlH_4/TiCl_x$ reaction mixture in tetrahydrofuran and the dioxolane are then combined at 20°-35° C. until dechlorination occurs. The time and pressure can readily be determined by one skilled in the art. Usually, room temperature is used for both reactions (Steps A and B). The resulting dioxole is then isolated, usually by distillation.

The dioxoles so produced by the process of this invention can be polymerized to form polymers which are useful as coating materials, in anti-corrosive devices, or as optical fiber clads.

EXAMPLES

EXAMPLE 1

Preparation of Perfluoro-2,2-Dimethyl-3-Dioxole

In a round-bottomed flask with two side-arms, equipped with a cooling condenser, a thermocouple and a rubber stopper, was charged lithium aluminum hydride (2.0 g, 0.0526 mole) and tetrahydrofuran (THF) solvent (40 mL) with cooling. Strong gas evolution was observed. The system was placed under nitrogen atmosphere and titanium tetrachloride (2.46 g, 1.43 mL, 0.013 mole) was introduced into the flask via a syringe through the rubber stopper. The system was stirred vigorously during this addition and kept below 15° C. by cooling in an ice-water bath.

The color of the solution turned yellow, then gradually black. After the addition the reagent mixture was allowed to stir without cooling for 25 minutes; then the flask was again placed in the ice-water bath and cooled to about 25° C. At this time 4,5-dichloro-4,5-difluoro-2,2-bis(trifluoromethyl)-1,3-dioxolane (8 g, 0.0254 mole) was added at a rate such that the reaction temperature was kept at 20° to 25° C. with external cooling.

After the addition was complete, the perfluoro-2,2-dimethyl-1,3-dioxole product was distilled out from the reaction mixture, and the THF solvent codistilled out was washed away with ice-water. The yield of this process over several runs ranged from 50 to 70%. The product had a boiling point of 33° C.

Comparative Example A

In this run, no titanium halide was present.

In a round-bottomed flask was charged lithium aluminum hydride (3.8 g, 0.1 mole) in tetrahydrofuran (75 mL) and the contents was cooled in an ice-water bath at 0° to 5° C. 4,5-Dichloro-4,5-difluoro-2,2-bis(trifluoromethyl)-1,3-dioxolane (31.5 g, 0.1 mole) was added slowly. After the addition was complete, the reaction mixture was stirred at room temperature for 30 minutes. The resulting mixture was neutralized with 4.8N HCl (50 mL), then poured into 300 mL of ice-water. The bottom layer was separated and washed twice with cold water (200 mL). Distillation gave the saturated product 4,5-difluoro-2,2-bis(trifluoromethyl)-1,3-dioxolane (17 g, 69% yield) instead of the unsaturated dioxole product.

Comparative Example B

In this run, the reaction temperature of Step B was too high and the molar ratio of $LiAlH_4$ to $TiCl_3$ was 1:2, as in Olah et al, supra.

In a round-bottomed flask, lithium aluminum hydride (0.50 g, 0.013 mole) was slowly added to a mixture to titanium trichloride (4.0 g, 0.0259 mole) and tetrahydrofuran (40 mL) under nitrogen with vigorous stirring. The resulting mixture was stirred for an additional 40 minutes, then 4,5-dichloro-4,5-difluoro-2,2-bis(trifluoromethyl)-1,3-dioxolane (8 g, 0.0254 mole) was introduced slowly into the mixture via a syringe. When the addition was complete, the reaction mixture was brought to reflux for 2 h. The volatile product was distilled out from the mixture, some starting material was recovered, and the yield of the desired product, perfluoro-2,2-dimethyl-1,3-dioxole was only about 15%.

EXAMPLE 2

Preparation of Perfluoro-2,2-Dimethyl-1,3-Dioxole

This example was carried out with lithium aluminum hydride (2.0 g, 0.052 mole), titanium trichloride (4.0 g, 0.026 mole) and 4,5-dichloro-4,5-difluoro-2,2-bis(trifluoromethyl)-1,3-dioxolane (8.0 g, 0.0254 mole) in tetrahydrofuran solvent (40 mL) the same way as described in Example 1. The conversion was 100% and the yield of perfluoro-2,2-dimethyl-1,3-dioxole was 45%.

EXAMPLE 3

Preparation of Perfluoro-2,2-Dimethyl-1,3-Dioxole

This example was conducted in the same manner as Example 1, except that the reactants were the following: Lithium aluminum hydride (8.0 g, 0.211 mole), titanium tetrachloride (9.84 g, 0.052 mole), 4,5-dichloro-4,5-difluoro-2,2-bis(trifluoromethyl)-1,3-dioxolane (31.5 g, 0.1 mole) and tetrahydrofuran (100 mL). The yield of this reaction was 53% with 100% conversion.

EXAMPLE 4

Preparation of Perfluoro-2-Ethyl-1,3-Dioxole

To a 300 mL round-bottomed flask was charged lithium aluminum hydride (8.0 g, 0.211 mole) in THF (120 mL). Titanium (IV) chloride (9.84 g, 5.70 mL, 0.052 mole) was added with cooling. This mixture was heated to reflux for 30 minutes. After cooling to 30° C., the 4,5-dichloro-2,4,5-trifluoro-2-pentafluoroethyl-1,3-dioxolane (32.0 g, 0.102 mole) was introduced via a syringe while the temperature of the system was kept between 25° and 35° C. during the addition by cooling. After the addition was complete, the reaction mixture was stirred for an additional 5 to 10 minutes before distillation. 12.8 G (6.6 mL) of the desired product perfluoro-2-ethyl-1,3-dioxole (54% yield) was obtained: boiling point 40° C.

EXAMPLE 5

Preparation of Perfluoro-2-Ethyl-2-Methyl-1,3-Dioxole

This example was carried out as illustrated in Example 4 with lithium aluminum hydride (6.14 g, 0.162 mole), titanium (IV) chloride (7.67 g, 4.43 mL, 0.041 mole) and 4,5-dichloro-4,5-difluoro-2-pentafluoroethyl-2-trifluoromethyl-1,3-dioxolane (29.5 g, 0.081 mole) in tetrahydrofuran (100 mL). The pure desired product obtained after distillation and washing with ice-water, perfluoro-2-ethyl-2-methyl-1,3-dioxole, was 9.0 g (38% yield); boiling point 42°–43° C.

EXAMPLE 6

Preparation of Perfluoro-2,2-Diethyl-1,3-Dioxole

This example was conducted in a manner similar to that described in Example 4 with the following reagents: lithium aluminum hydride (6.59 g, 0.173 mole), titanium tetrachloride (8.23 g, 4.76 mL, 0.0434 mole), THF (110 mL) and 4,5-dichloro-4,5-difluoro-2,2-bis(pentafluoroethyl)-1,3-dioxolane (36 g, 0.087 mole). The yield of the desired product perfluoro-2,2-diethyl-1,3-dioxole was 13 g (44%) after purification: boiling point 52° C.

EXAMPLE 7

Preparation of 2,2-Bis(Chlorodifluoromethyl)-4,5-Difluoro-1,3-Dioxole

This example was performed as described in Example 4 with lithium aluminum hydride (7.6 g, 0.2 mole), titanium tetrachloride (9.5 g, 5.48 mL, 0.05 mole) and 4,5-dichloro-4,5-difluoro-2,2-bis(chlorodifluoromethyl)-1,3-dioxolane (34.8 g, 0.1 mole) in THF (130 mL). The desired product, 2,2-bis(chlorodifluoromethyl)-4,5-difluoro-1,3-dioxole, was identified in the THF solution by gas chromatography and its $^{19}F$ NMR spectrum ($CFCl_3$ as external standard): −67.9 (s, 4F), −159.4 (s, 2F).

EXAMPLE 8

Preparation of Perfluoro-2,2,4-Trimethyl-1,3-Dioxole

The reagent mixture was prepared from lithium aluminum hydroxide (2.5 g, 0.066 mole) and titanium (IV) chloride (3.12 g, 1.80 mL, 0.016 mole) in THF (40 mL) as illustrated previously. 4,5-Dichloro-2,2,4-tris(trifluoromethyl)-1,3-perfluoro dioxolane (12.0 g, 0.033 mole) was introduced into the dechlorination reagent at the temperature 27° to 35° C. After the routine work-up procedure, 8.5 g (88% yield) of pure desired product, perfluoro-2,2,4-trifluoromethyl-1,3-dioxole, was obtained as a clear colorless oil; boiling point 42° C. $^{19}$F NMR (neat, CFCl$_3$ as external standard): −68.6 (d, J=11.5 Hz, 3F), −84.2 (s, 6F), −136.8 (q, J=11.5 Hz, 1F).

EXAMPLE 9

Preparation of Perfluoro-2-Propyl-1,3-Dioxole

The title compound was prepared in accordance with previously described procedures. The desired product was identified from the product mixture after distillation by gas chromatography and the $^{19}$F NMR spectrum (in THF solution, CFCl$_3$ as external standard): −82.0 (m, 3F), −126.0 (m, 2F), −71.0 (m, 1F), −159.8 (d, J=3 Hz, 2F).

What is claimed:

1. Dechlorination process for preparing the dioxole of the formula

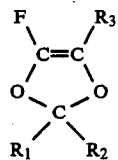

wherein R$_1$ and R$_2$ are each independently selected from the class consisting of fluorine, chloroalkyl, chlorofluoroalkyl and fluoroalkyl of 1–3 carbon atoms, and R$_3$ is F, Cl or perfluoroalkyl of 1–3 carbon atoms, which process comprises:

A. adding LiAlH$_4$ and TiCl$_x$ wherein x is 3 or 4 to tetrahydrofuran at a molar ratio of LiAlH$_4$ to TiCl$_x$ of 2:1 to 8:1, and mixing the components at 0° C. to the reflux temperature of the mixture for 15–120 minutes;

B. mixing the dioxolane of the formula

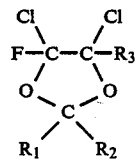

wherein R$_1$, R$_2$ and R$_3$ are as defined above into the mixture prepared in Step A until the molar ratio of the dioxolane to TiCl$_x$ is 1:1 to 4:1, at a temperature of 20°–35° C.; and C. isolating from Step B the dioxole of the aforesaid formula formed.

2. The process of claim 1 wherein the dioxolane is 4,5-dichloro-4,5-difluoro-2,2-bis(trifluoromethyl)-1,3-dioxolane.

3. The process of claim 1 wherein the dioxolane is 4,5-dichloro-5-fluoro-2,2,4-tris(trifluoromethyl)-1,3-dioxolane.

* * * * *